United States Patent
Sato et al.

(10) Patent No.: US 6,792,791 B2
(45) Date of Patent: Sep. 21, 2004

(54) INSPECTION CHIP FOR SENSOR MEASURING INSTRUMENT

(75) Inventors: Yoshiharu Sato, Kyoto (JP); Masufumi Koike, Kyoto (JP); Yasuhito Kawamata, Ehime (JP); Yoshinobu Tokuno, Ehime (JP)

(73) Assignees: Matsushita Electric Industrial Co., Ltd., Osaka (JP); Arkray, Inc., Kyoto (JP)

( * ) Notice: Subject to any disclaimer, the term of this patent is extended or adjusted under 35 U.S.C. 154(b) by 0 days.

(21) Appl. No.: 09/958,886

(22) PCT Filed: Feb. 19, 2001

(86) PCT No.: PCT/JP01/01152

§ 371 (c)(1),
(2), (4) Date: Dec. 12, 2001

(87) PCT Pub. No.: WO01/61342

PCT Pub. Date: Aug. 23, 2001

(65) Prior Publication Data

US 2002/0152793 A1 Oct. 24, 2002

(30) Foreign Application Priority Data

Feb. 18, 2000 (JP) ........................................ 2000-041716

(51) Int. Cl.[7] ............................................. G01N 21/00
(52) U.S. Cl. ....................................................... 73/1.02
(58) Field of Search ............................................ 73/1.02

(56) References Cited

U.S. PATENT DOCUMENTS

| 3,783,345 | A | * | 1/1974 | Taylor et al. ............ 317/234 R |
| 4,366,241 | A | * | 12/1982 | Tom et al. .................... 435/7 |
| 5,266,179 | A | * | 11/1993 | Nankai et al. ............. 204/401 |
| 5,284,770 | A | * | 2/1994 | Adrian et al. ................ 436/8 |
| 5,438,271 | A | * | 8/1995 | White et al. ................ 324/444 |
| 5,526,120 | A | * | 6/1996 | Jina et al. ................... 356/446 |
| 5,872,713 | A | | 2/1999 | Douglas et al. |
| 5,873,990 | A | * | 2/1999 | Wojciechowski et al. ... 204/406 |
| 5,995,236 | A | * | 11/1999 | Roth et al. .................. 356/445 |
| 6,009,632 | A | * | 1/2000 | Douglas ...................... 33/562 |
| 6,066,847 | A | * | 5/2000 | Rosenthal ............ 250/252.1 R |
| 6,377,894 | B1 | * | 4/2002 | Deweese et al. .............. 702/22 |
| 6,544,475 | B1 | * | 4/2003 | Douglas et al. ............... 422/61 |
| 2001/0039057 | A1 | * | 11/2001 | Douglas et al. |

FOREIGN PATENT DOCUMENTS

| AU | 9851575 | 5/1998 |
| DE | 297 20 299 | 1/1998 |
| DE | 29723400 | 9/1998 |
| DE | 19781162 | 3/1999 |
| DE | 29723665 | 3/1999 |

(List continued on next page.)

*Primary Examiner*—Hezron Williams
*Assistant Examiner*—Charles Garber
(74) *Attorney, Agent, or Firm*—Wenderoth, Lind & Ponack, L.L.P.

(57) ABSTRACT

A check chip of the present invention employed at a usage of a sensor measuring device is provided with a structural characterizing portion of a convex shape, concave shape or a penetration hole at a location, by which a user is considered to pick up, and the state of the structural characterizing portion is made to be different from that of a structural characterizing portion provided on a correction chip which is similar to the check chip, in a size, the number of the structural characterizing portions, or placement location.

According to the check chip constructed as above, the difference from the correction chip can be easily identified even by a visually handicapped person or a weak-sighted person, according to the difference in the structural characterizing portion, from the touch, thereby preventing the person from using the check chip and the correction chip with confused.

9 Claims, 4 Drawing Sheets

FOREIGN PATENT DOCUMENTS

| | | | | |
|---|---|---|---|---|
| EP | 001172653 A1 * | 1/2002 | .......... | G01N/33/48 |
| GB | 2 159 625 | 12/1985 | | |
| GB | 2322444 | 8/1998 | | |
| JP | 58-4981 | 1/1983 | | |
| JP | 61-294351 | 12/1986 | | |
| JP | 4-181159 | 6/1992 | | |
| JP | 4-188065 | 7/1992 | | |
| JP | 4-357452 | 12/1992 | | |
| JP | 8-20412 | 3/1996 | | |
| JP | 11-510915 | 9/1999 | | |
| WO | 98/19519 | 5/1998 | | |

* cited by examiner

Fig.1 direction along which a chip is inserted in a measuring device →

Fig.2 direction along which a chip is inserted in a measuring device →

Fig.7(a)
PRIOR ART direction along with a chip is inserted in a measuring device →

Fig.7(b)
PRIOR ART direction along with a chip is inserted in a measuring device →

INSPECTION CHIP FOR SENSOR MEASURING INSTRUMENT

FIELD OF THE INVENTION

The present invention relates to a check chip for performing an operative validation of a sensor measuring device for assaying a specified component in a liquid sample, and more particularly, to a check chip which can be easily distinguished from a sensor having a similar shape, which is employed in the sensor measuring device, by a visually handicapped user or a weak-sighted person.

BACKGROUND OF THE INVENTION

In recent years, a low-priced sensor for assaying a specified component in a liquid and a measuring device exclusively employed for reading a quantitative change in the specified component within the sensor have been developed and adopted in the clinical field.

For example, when it is cited as an example that the measuring object is glucose, there are proposed a disposable sensor for detecting an electrochemical potential difference, which comprises a specific catalysis of an enzyme and an electrode, and a measuring device exclusively employed for reading a quantitative change within the sensor, so that diabetic patients can measure and control blood sugar levels by themselves. Further, in a case where the measuring object is potassium ion or sodium ion, there are proposed a disposable ion selective electrode sensor for assaying ions in a liquid, which comprises an ion selecting film and a reference electrode, and a measuring device exclusively employed for reading a quantitative change within the sensor. As a principle applied to these disposable sensors, there is optical measurement besides the above-described electrochemical reaction.

Further, there is a measuring device which announces the measurement result of blood sugar level or ion concentration which is measured as described above, by voice or the like, whereby a visually handicapped user or a weak-sighted person can use the device with no difficulties.

As a disposable sensor which comprises a specific catalysis of an enzyme and an electrode, there is a sensor disclosed in Japanese Published Patent Application No. Sho. 61-294351. This sensor is constituted by forming electrode circuitry on an insulating plate with a printing method, and covering the electrode circuitry with madreporic body containing an oxidation-reduction enzyme and an election acceptor, thereby to integrate the whole with a cover. Therefore, the component in the biological sample can be measured as a substrate by appropriately selecting the type of the oxidation-reduction enzyme contained in the madreporic body. When a sample is applied to the sensor, the electron acceptor is deoxidized by the enzyme reaction. At this time, a predetermined voltage is applied to the electrode circuitry, whereby the deoxidized electron acceptor is oxidized electrochemically by the voltage, oxidation current flows between electrodes, and the substrate component concentration in the sample can be measured from the oxidation current value.

Further, an ion selective electrode sensor generally comprising a reference electrode, an electrolyte layer, and an ion selective film is disclosed in Japanese Examined Patent Application No. 58-4981. The disclosed ion selective electrode is constituted by depositing a metal layer on a plastic film, and coating or laying the electrolyte layer and the ion selective film thereon.

Further, a sensor and a sensor measuring device employing optical detection as a principle are disclosed in Japanese Published Patent Application No. Hei. 4-188065. This sensor, which employs optical detection as a principle, has a capillary tube shape, a part of which has optical penetrability. A dry reagent is applied in the capillary tube, and the sensor measuring device optically measures a change in color tone which is generated when the liquid sample and the reagent, which are introduced into the capillary tube, react to each other, through the optical penetrability portion, to calculate the concentration of a specific component contained in the liquid according to the color tone.

Further, when a diabetic patient measures sugar level by himself using the above-described sensor and measuring device for the sensor, a device and a method by which the patient can easily perform calibration or certification of the measuring device are disclosed in Japanese Examined Patent Application No. Hei. 8-20412. To be specific, the sensor and the measuring device utilize the fact that the resistance value of the sensor decreases sharply when the liquid sample is supplied to the sensor, and the sensor measuring device detects the change in the resistance value in the sensor to automatically start the measurement, whereby variations in the measurement results due to variations in the measurement start operations by users are avoided. Further, an adjustment chip having a constant resistance value, which chip is similar in shape to the above-described sensor, is formed, and when a measuring sensor and an adjustment sensor (adjustment chip) are loaded to the measuring device, the measuring device automatically distinguishes the measuring sensor from the adjustment sensor according to a difference in resistance values between these two sensors, thereby automatically adjusting, calibrating or examining the measuring device.

Among the adjustment chips, there are, for example, two types of chips as adjustment chips to be used by a patient himself as follows.

1. A correction chip for adjusting errors in analytical curves or the like, which occur due a lot change of materials, every time a patient buys sensors by a box.

2. A check chip for performing an operative validation of a measuring device itself, which is employed only when a patient buys a new device.

The above-mentioned materials denote components which may vary due to a lot change. For example, when the employed sensor comprises an enzyme electrode, there may be lot-to-lot variations in an enzyme or an electrode material, when the sensor comprises an ion selective electrode, there may be lot-to-lot variations in an ion selective film material or a metal foil used for the electrode, and when the sensor adopts optical detection, there may be lot-to-lot variations in a reagent ingredient or an optical element. Therefore, all sensor measuring devices employing sensors require adjustment chips suitable to the respective detection principles although the detection principles are different from each other.

Figure 7A:
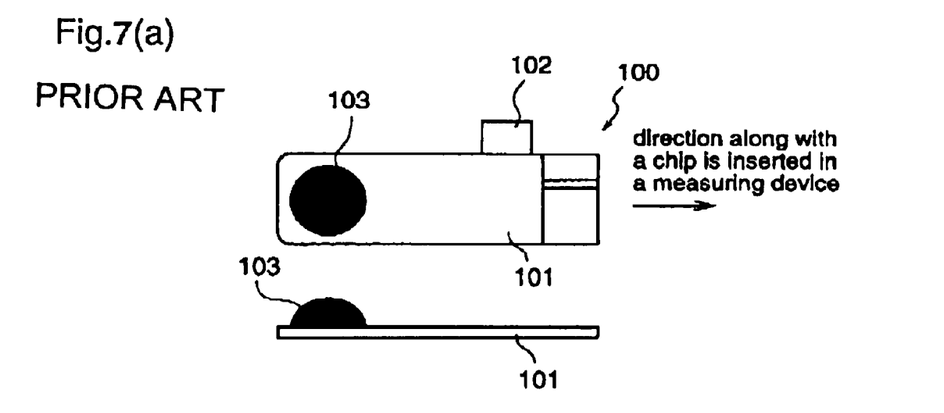
FIGS. 7(a) and (b) show plan views and side views illustrating a check chip and a correction chip according to prior art.
Figure 7B:
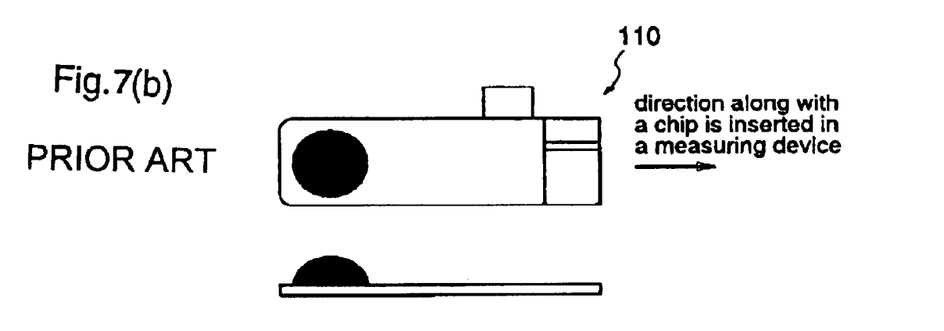

However, both of the two adjustment chips, i.e., the correction chip and the check chip, are usually similar in shape to the measuring sensor used for the measurement. FIGS. 7(a) and (b) show plan views and side views illustrating a check chip and a correction chip according to prior art. For example, when taking, as an example, a correction chip 100 using a resistance value as a target of correction, as shown in FIGS. 7(a) and (b), this correction chip is generally constituted by a sensor body 10, an incorrect insertion preventing projection 102 to be a protrusion for preventing the sensor from being inserted into a measuring device while mistaking the inside of the sensor for the outside, and a convex-shaped structural characterizing portion 103 which is swelled because a resistor is buried therein. As shown in FIGS. 7(a) and (b), since the correction chip 100 and the check chip 110 are especially similar to each other in shape, these chips are easily confused with each other due to the similarity in the shape. Accordingly, when a visually handicapped person or a weak-sighted person uses the correction chip 100 or the check chip 110, the possibility that the two chips are erroneously used is very high.

The present invention is made to solve the problems and has an object to provide a check chip for performing an operative validation of a sensor measuring device, which can be easily distinguished from a correction chip for adjusting errors even by a visually handicapped user.

DISCLOSURE OF THE INVENTION

According to the present invention, there is provided a check chip which is installed on a measuring device employing an exclusively used sensor and checks operations of the measuring device itself, wherein the check chip is provided thereon with at least one structural characterizing portion which makes a user of the measuring device recognize a difference from a correction chip for correcting errors that occur with lot changes in the exclusively used sensor.

Therefore, it is possible to provide a check chip, in which a difference from the correction chip can be easily detected, so that it is possible to prevent confusion when using the check chip and the correction chip.

According to the present invention, in the check chip, the structural characterizing portion has a shape, such as a convex shape, which can be recognized by the user from touch, and is provided in a location where the user is considered to pick up the check chip.

Therefore, it is possible to provide a check chip, in which a difference from the correction chip can be detected with touch, so that even a visually handicapped person or a weak-sighted person can detect a difference from the correction chip.

According to the present invention, in the check chip, a difference between the check chip and the correction chip resides in a size of the structural characterizing portion, when the correction chip has the structural characterizing portion.

Therefore, it is possible to provide a check chip in which a difference between the check chip and the correction chip can be detected in the size of the structural characterizing portion with touch, and even a visually handicapped person or a weak-sighted person can easily detect the difference from the correction chip.

According to the present invention, in the check chip, the size of the structural characterizing portion provided on the check chip is larger than that of the structural characterizing portion provided on the correction chip.

Therefore, it is possible to provide a check chip in which a person can detect, with touch, that the structural characterizing portion of the check chip is larger than that of the correction chip, so as to detect the difference from the correction chip, whereby even a visually handicapped person or a weak-sighted person can be prevented from using the two chips with confusion. Further, the structural characterizing portion of the check chip, the usage frequency of which is lower than that of the correction chip, is enlarged, and therefore, manufacturing cost can be reduced.

According to the present invention, in the check chip, the size of the structural characterizing portion provided on the check chip is smaller than that of the structural characterizing portion provided on the correction chip.

Therefore, it is possible to provide a check chip in which a person can detect, with touch, that the structural characterizing portion of the check chip is smaller than that of the correction chip, so as to easily distinguish the difference from the correction chip, whereby it is possible to prevent a visually handicapped person or a weak-sighted person from using the two chips with confusion.

According to the present invention, the check chip is provided with the structural characterizing portion on the both sides of the check chip.

Therefore, it is possible to provide a check chip in which the difference between the check chip and the correction chip can be detected with touch, according to the mounted place of the structural characterizing portion, whereby the difference from the correction chip can be detected easily even by a visually handicapped person or a weak-sighted person.

According to the present invention, in the check chip, a difference between the check chip and the correction chip resides in a number of the structural characterizing portions.

Therefore, it is possible to provide a check chip in which the difference between the check chip and the correction chip can be detected with touch, according to the number of the structural characterizing portions, whereby the difference from the correction chip can be detected easily even by a visually handicapped person or a weak-sighted person.

According to the present invention, in the check chip, the number of the structural characterizing portions provided on the check chip is larger than that of the structural characterizing portions provided on the correction chip.

Therefore, it is possible to provide a check chip in which a person can detect, with touch, that the number of the structural characterizing portions of the check chip is larger than that of the structural characterizing portions of the correction chip, so as to easily detect the difference from the correction chip, whereby it is possible to prevent a visually handicapped person or a weak-sighted person from using the two chips with confusion. Further, the number of the structural characterizing portions of the check chip, the usage frequency of which is lower than that of the correction chip, is enlarged, and therefore, manufacturing cost can be reduced.

According to the present invention, in the check chip, the number of the structural characterizing portions provided on the check chip is smaller than that of the structural characterizing portions provided on the correction chip.

Therefore, it is possible to provide a check chip in which a person can detect, with touch, that the number of the structural characterizing portions of the check chip is smaller than that of the structural characterizing portions of the correction chip, so as to easily detect the difference from the correction chip, whereby it is possible to prevent a visually handicapped person or a weak-sighted person from using the two chips with confusion.

According to the present invention, in the check chip, a structural characterizing portion on an attention attracting character printed on an upside of the check chip, among plural structural characterizing portions provided on the check chip, has optical penetrability.

Therefore, it is possible to make the attention attracting character readable, even when the attention attracting character printed on the chip which indicates a type of the chip is hidden under the structural characterizing portion on the ground that the number of the structural characterizing portions is large, whereby even a person having a good sight who does not know a detection method according to the structural characterizing portions of the both chips can easily distinguish the two chips from each other.

According to the present invention, in the check chip, a difference between the check chip and the correction chip resides in the shape of the structural characterizing portion.

Therefore, it is possible to provide a check chip, in which a person can detect, with touch, the difference between the check chip and the correction chip according to the shape of the structural characterizing portions, whereby even a visually handicapped person or a weak-sighted person can easily distinguish the difference from the correction chip.

DETAILED DESCRIPTION OF THE PREFERRED EMBODIMENTS

Embodiment 1

Hereinafter, a description will be given of a check chip for checking operations of a measuring device in which a difference from a correction chip for correcting is clarified by a structural characterizing portion 3, with reference to FIGS. 1 to 6, according to a first embodiment of the present invention. The correction chip and the check chip are executed in contrast to resistance value in a resistor buried in a sensor body 1 that has an incorrect insertion preventing projection 2 to prevent the chip from being incorrectly inserted into a measuring device.

Figure 1:
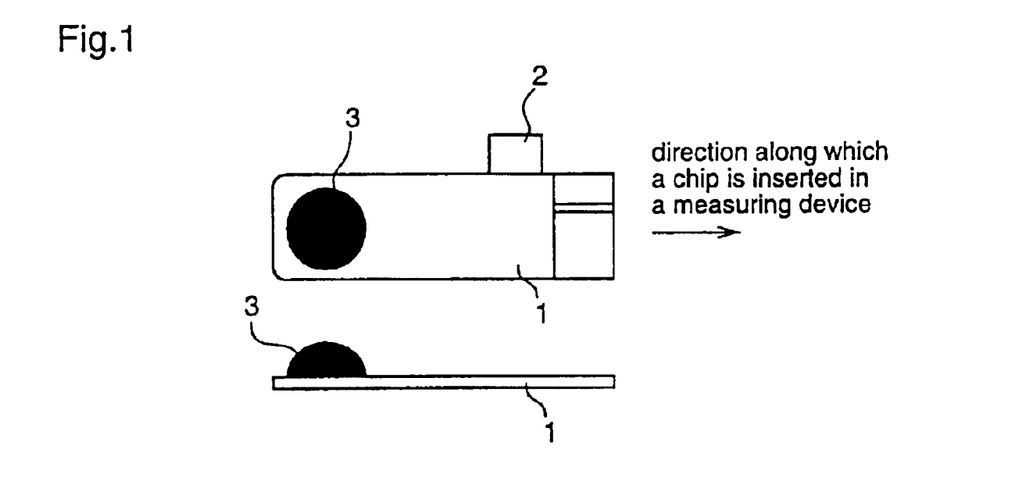
FIG. 1 is a plan view and a side view illustrating a shape of a general correction chip employed in a sensor measuring device according to a first embodiment of the present invention.

FIG. 1 shows a plan view and a side view illustrating a correction chip having a circular convex shaped structural characterizing portions on an upside of a sensor body according to the first embodiment of the present invention.

In this first embodiment, a description will be given with citing as an example, a type, in which the structural characterizing portion 3 both of the correction chip and the check chip is convex shaped. Though, the shape of the structural characterizing portion 3 might be concave shaped or penetrations in the sensor body 1, which can be recognized by a user with the touch. When the structural characterizing portion 3 has a convex shaped, it is ideal for the operation, since a resistor can be buried in this convex portion.

Initially, a description will be given in a case where the difference between the check chip and the correction chip resides in a size of the structural characterizing portion 3.

Figure 2:
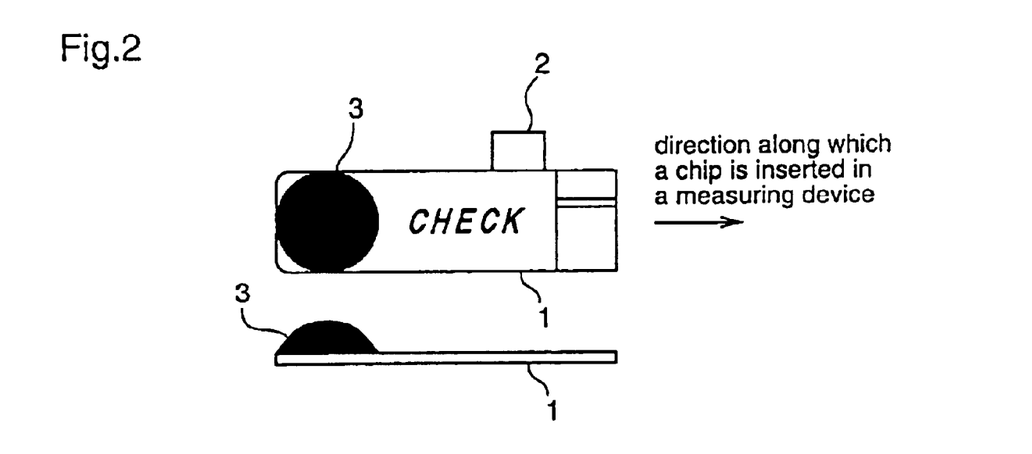
FIG. 2 shows a plan view and a side view illustrating a check chip having a structural characterizing portion of a large diameter according to the first embodiment of the present invention.

FIG. 2 shows a plan view and a side view illustrating a check chip, in which a diameter of the structural characterizing portion 3 having a circular convex shaped is equal to the sensor body 1, according to the first embodiment of the present invention. In FIG. 2, the same reference numerals and characters as those in FIG. 1 designate the same or corresponding parts. So, the descriptions will be omitted.

The structural characterizing portion 3 of the correction chip shown in FIG. 1 has a diameter which is smaller than a width of the sensor body 1. In contrast thereto, the circular convex shaped structural characterizing portion 3 of the check chip according to this embodiment has a diameter which is equal to width of the sensor body 1, as shown in FIG. 2. As described above, a size of the structural characterizing portion 3 of the check chip is made to differ from that of the structural characterizing portion 3 of the correction chip, thereby to distinguish the both chips from each other not only from their appearances but also from their touch.

As for the size of the structural characterizing portion 3, the check chip may have larger one than that of the correction chip as described above, or, on the contrary, the correction chip may have larger one than that of the check chip (not shown). However, when considering that the correction chip, which is required whenever measuring sensors are bought by a box, is used more frequently than the check chip, which is required only when a measuring device is newly bought, and that the number of the correction chips is larger than that of the check chip, it is more desirable that the structural characterizing portion 3 of the check chip is larger than that of the correction chip in view of a large number of the manufactured correction chips.

Further, the difference between the check chip and the correction chip may reside in the placement location of the structural characterizing portion 3, as shown in FIGS. 1 to 3(b).

Figure 3A:
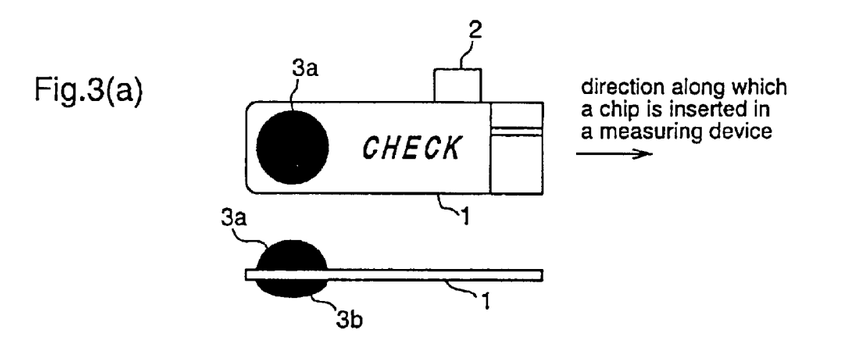
FIGS. 3(a) and (b) show plan views and side views illustrating a check chip having structural characterizing portions which are provided on both sides thereof according to the first embodiment of the present invention.
Figure 3B:
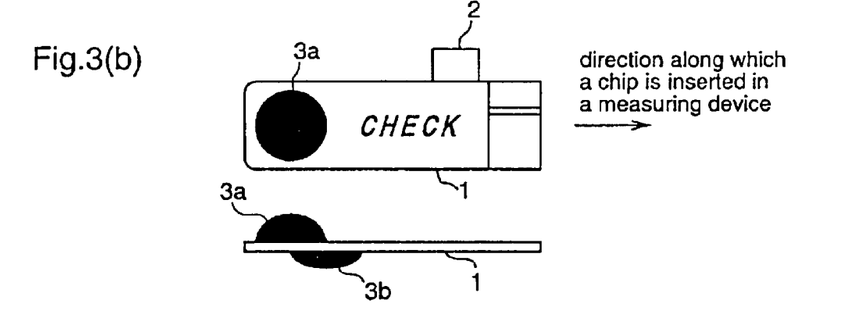

FIGS. 3(a) and 3(b) are plan views and side views illustrating check chips having circular convex shaped structural characterizing portions on both surfaces of the sensor body according to the first embodiment of the present invention. FIG. 3(a) illustrates that placement locations of the respective structural characterizing portions on both surfaces correspond to each other, and FIG. 3(b) illustrates that the placement locations of the respective structural characterizing portions do not correspond to each other. In FIGS. 3(a) and (b), reference numeral 3a designates a structural characterizing portion placed on the upside of the sensor body 1, and reference numeral 3b designates a structural characterizing portion placed on the downside of the sensor body 1. Further, the same reference numerals and characters as those in FIG. 1 designate the same or corresponding parts. So, the descriptions will be omitted.

Here, the structural characterizing portion 3 of the correction chip shown in FIG. 1 is provided only on the upside of the sensor body 1. In contrast thereto, according to the check chip of the first embodiment, the circular convex shaped structural characterizing portions 3a and 3b of are provided on both sides of the sensor body 1, as shown in FIGS. 3(a) and (b). As described above, placement location of the structural characterizing portion 3 of the check chip is made to be different from the placement location of the structural characterizing portion 3 of the correction chip, thereby both chips can be distinguished from each other not only from their appearances but also their feel.

Further, in the check chip, the respective locations of the structural characterizing portions 3a and 3b which are provided on both sides of the sensor body 1 may correspond to each other as shown in FIG. 3(a), or the respective locations are different from each other as shown in FIG. 3(b).

As for the placement location of the structural characterizing portion 3, the check chip may have the structural characterizing portions 3 on both sides of the sensor body 1 and the correction chip may have the same only on an upside of the sensor body 1 as described above, or the contrary case (not shown) may be accepted. However, in view of the above-described difference in the number of chips that are, it is more desirable in the manufacturing that the check chip have the structural characterizing portions 3a and 3b on both sides of the sensor body 1.

Further, the difference between the check chip and the correction chip may resides in the number of the structural characterizing portions 3, as shown in FIGS. 1 to 4(b).

Figure 4A:
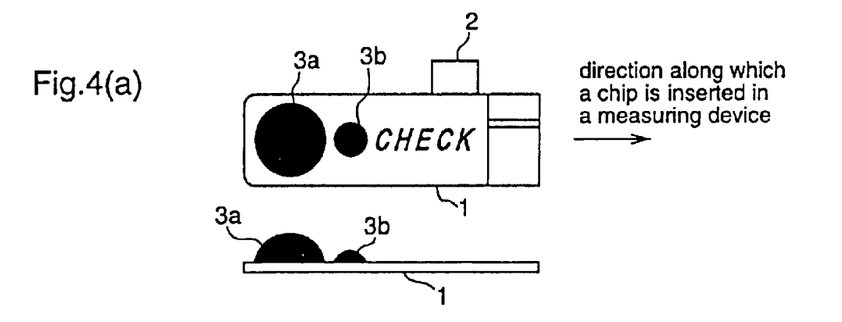
FIGS. 4(a) and (b) show plan views and side views illustrating a check chip having plural pieces of structural characterizing portions according to the first embodiment of the present invention.
Figure 4B:
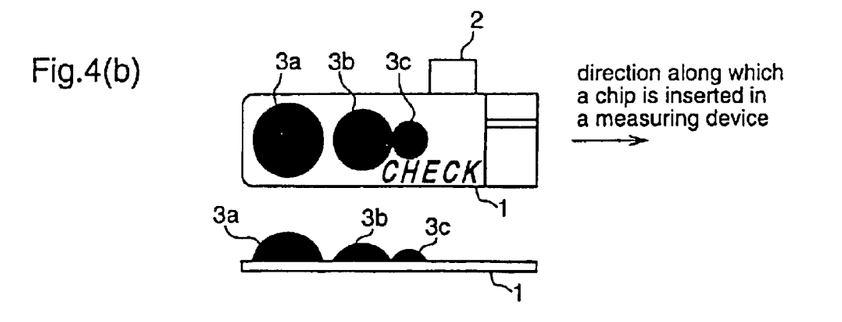

FIGS. 4(a) and 4(b) are plan views and side views illustrating check chips having plural circular convex shaped structural characterizing portions according to the first embodiment of the present invention. FIG. 4(a) illustrates a check chip having two structural characterizing portions on the upside of the sensor body 1, and FIG. 4(b) illustrates a check chip having three structural characterizing portions. In FIGS. 4(a) and (b), reference numerals 3a, 3b and 3c designate structural characterizing portions which are provided adjacent to each other on the upside of the sensor body 1, and the same reference numerals and characters as those in FIG. 1 designate the same or corresponding parts. So, the descriptions will be omitted.

Here, only one structural characterizing portion 3 of the correction chip shown in FIG. 1 is provided on the upside of the sensor body 1. In contrast thereto, according to the check chip of the first embodiment, the circular convex shaped structural characterizing portions 3a and 3b are provided adjacent to each other on the upside of the sensor body 1, as shown in FIG. 4(a). As described above, the number of the structural characterizing portions 3a and 3b are made to be different from the number of the structural characterizing portion 3 of the correction chip, whereby both chips can be distinguished from each other not only from their appearances, but also from their feel.

Further, according to the check chip, the number of the structural characterizing portions provided may be either two as shown in FIG. 4(a) or three as shown in FIG. 4(b), if the structural characterizing portions can be constituted on the sensor body 1.

Further, the number of the structural characterizing portions 3 of the check chip may be larger than that of the structural characterizing portion 3 of the correction chip, as described above, or the contrary case (not shown) can be accepted. However, in view of a difference in the number of the manufactured products of both chips, it is more desirable in the manufacturing that the number of the structural characterizing portions of the check chips is larger than that of the structural characterizing portion of the correction chip.

Further, the respective sizes of the plural structural characterizing portions 3 of the check chip may be all the same, or there may be some differences between the structural characterizing portions 3a, 3b and 3c as shown in FIGS. 4(a) and 4(b). However, when three or more structural characterizing portions are provided on the upside of the sensor body 1, it is desirable, in view of limited area of the sensor body 1, that only the structural characterizing portion 3a containing a resistor is enlarged and other structural characterizing portions 3b and 3c are diminished, as shown in FIG. 4(b).

Figure 5:
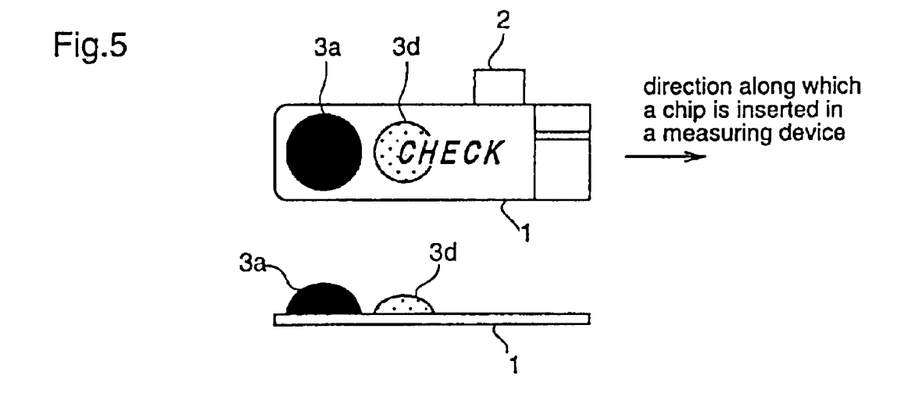
FIG. 5 shows a plan view and an elevation view illustrating a check chip in which a portion of plural structural characterizing portions has optical penetrability according to the first embodiment of the present invention.

Further, a part of the plural circular convex shaped structural characterizing portions 3 described with reference to FIGS. 4(a) and (b) may be optical penetrability, as shown in FIG. 5.

FIG. 5 is a plane view and a side illustrating a check chip, in which a part of the plural circular convex shaped structural characterizing portions is optical penetrability, according to the first embodiment of the present invention. In FIG. 5, reference numeral 3d designates a circular convex shaped structural characterizing portion having optical penetrability. The same reference numerals and characters as those in FIGS. 4(a) and (b) designate the same or corresponding parts. So, the descriptions will be omitted.

The sensor and measuring device employed in this first embodiment are often used by a person having good sight, and a person having good sight frequently assists a visually handicapped person in using a sensor measuring device. Therefore, many chips are printed on their surfaces with attention attracting characters indicating what the chip is used for, such as "for checking" or "CHECK", so as to indicate that the chips are check chips. In this case, when the check chip is provided with a structural characterizing portion 3 which is different from that of the correction chip, reading of the attention attracting character might be interrupted, especially in a case where the number of the structural characterizing portion 3 is large. Therefore, in order to enable a person having a good sight, who does not know a distinction means using the structural characterizing portions 3 of the both chips, to distinguish them from each other, one structural characterizing portion 3d out of the structural characterizing portions 3a and 3d is constituted to have optical penetrability as shown in FIG. 5, whereby the attention attracting character can be read out even if the attention attracting character printed on the sensor body 1 is hidden under the structural characterizing portion 3.

Figure 6A:
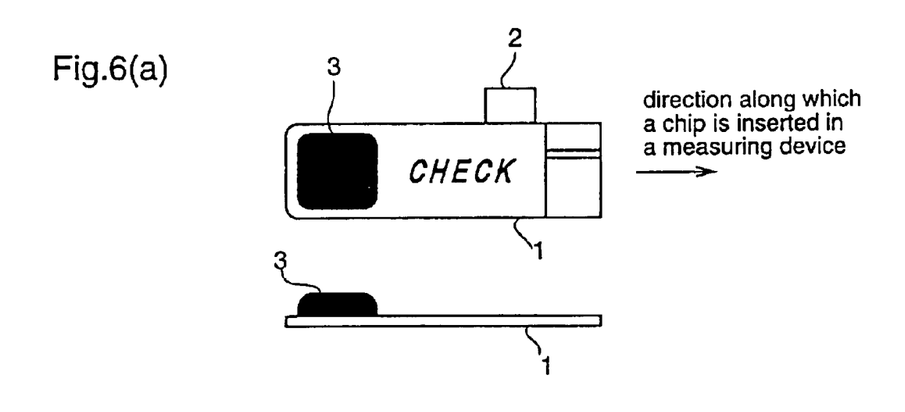
FIGS. 6(a) and (b) show plan views and side views illustrating check chips having different shapes from a correction chip according to the first embodiment of the present invention.
Figure 6B:
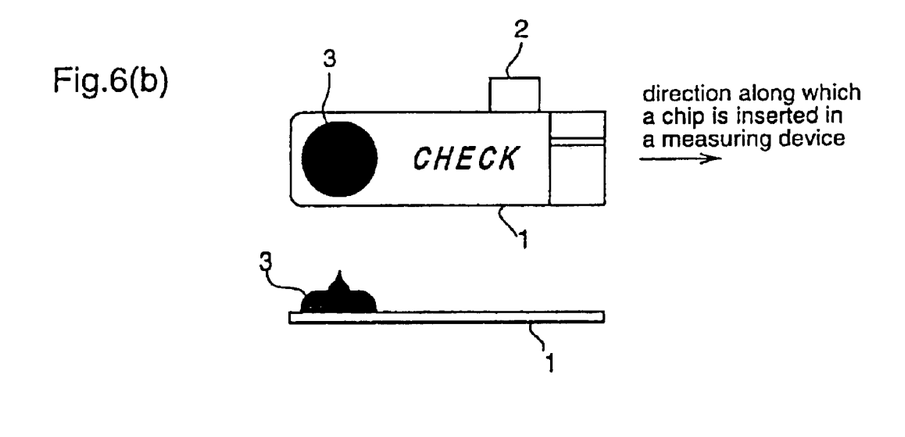

Further, difference between the check chip and the correction chip may reside in the shape of the structural characterizing portion 3, as shown in FIGS. 1 and 6(a) and (b).

FIGS. 6(a) and 6(b) are plane views and side views of check chips in which the shape of convex shaped structural characterizing portions is different from that of the structural characterizing portion of the correction chip, according to the first embodiment of the present invention. FIG. 6(a) is a view illustrating that the shape of a structural characterizing portion is rectangular convex shaped, and FIG. 6(b) is a view illustrating that the shape of a structural characterizing portion is circular convex shaped with an acute projection. In FIGS. 6(a) and (b), the same reference numerals and characters as those in FIG. 1 designate the same or corresponding parts. So, the descriptions will be omitted.

Here, the structural characterizing portion 3 of the correction chip shown in FIG. 1 has a circular convex shaped and gentle dome liked shape. In contrast thereto, the structural characterizing portion 3 of the check chip according to this first embodiment, for example, has circular convex shape with the acute projection, as shown in FIG. 6(b). Therefore, the shape of the structural characterizing portion 3 of the check chip is made to be different from that of the structural characterizing portion 3 of the correction chip, and the user can distinguish the check chip from the correction chip not only by their appearances, but also by their feel.

Further, the check chip of the first embodiment may a structural characterizing portion 3 which is constituted by combining the shapes of the structural characterizing portions 3 described with reference to FIGS. 2 to 5. For example, a desirable combination can be obtained such that plural structural characterizing portions 3 provided on the upside of the sensor body 1 are triangular or rectangular shaped, the structural characterizing portions 3 provided on both sides of the sensor body 1 are triangular or square shaped, or a correction chip has a convex shaped portion, in contrast to a check chip having a concave shaped portion.

Next, material for composing the structural characterizing portion 3 and methods for forming the same will be described.

Since a resistor which indicates constant value is contained in the structural characterizing portion 3 both in the check chip and in the correction chip, resin is employed for insulation in the structural characterizing portion 3. As a type of resin, the epoxy type resin is desirable. Further, it might be necessary to provide viscosity to the resin in order to form the desirable shape for the structural characterizing portion 3, and as thickener additive for adjusting the viscosity, silica powder is desirable.

Further, when assuming that the structural characterizing portions 3 both of the check chip and the correction chip are approximate circular shaped, it is desirable that their diameters have a size which is not larger than a width of the sensor body 1. Since the both chips are made to correspond to the measuring sensor in shape, in the case of a chip having approximately a 6 mm width, for example, it is desirable that a diameter of the approximate circular shaped structural characterizing portion 3 is smaller than 6 mm in its maximum. Further, the minimum value of the diameter is not especially limited, though, it is desirable that the diameter is 1 mm or more because a resistor is to be buried in the structural characterizing portion 3. When a smaller resistor is employed, the structural characterizing portion 3 can be further decreased in size. However, a size, with which a visually handicapped user can distinguish whether a sensor is a correction sensor or a check sensor from touch, is required.

A general forming method for the structural characterizing portion 3 containing a resistor employs conventional printing technique. More particularly, the structural characterizing portion 3 is piled up on the resistor by adjusting the thickness of a masking base material and the viscosity of the resin, via the masking material, with a penetration hole of a desirable diameter.

On the other hand, according to a forming method for the check chip having one structural characterizing portion 3a containing a resistor therein and plural structural characterizing portions 3b containing no resistor therein as shown in FIG. 4(a), since the structural characterizing portions 3b having no resistors therein do not require insulation, the insulation material is not necessary to be employed in the portions 3b. However, in view of convenience in the manufacturing, it is desirable that the structural characterizing portions 3b are produced with the same material as used in the structural characterizing portion 3a containing a resistor therein, employing the applied printing technique, In view of the low-frequency of the check chip, a check chip which is similar to the correction chip in shape is manufactured by employing the applied printing technique, and then the structural characterizing portions 3b containing no resistor are manually formed, using a syringe fill of the resin and an injection needle, thereby producing the check chip shown in FIG. 4(a).

As described above, according to the first embodiment of the present invention, the structural characterizing portion 3 of the correction sensor is different from that of the check sensor in shape, and further, the difference in the shape of the structural characterizing portion 3 is formed so as to be identified by a user from touch, and therefore, even a visually handicapped user can easily distinguish the correction chip from the check chip, so as to prevent the user from using the two chips with confusion.

Industrial Availability

The check chip for a sensor device of the present invention is extremely useful as one which can be easily distinguished even by a visually handicapped user from a correction chip having similar shape to the check chip, the correction chip being used for correcting at the time of lot change of a sensor.

What is claimed is:

1. A check chip to be mounted on a measuring device to check operations of the measuring device, said check chip comprising a sensor body with at least one structural characterizing portion provided thereon, said at least one structural characterizing portion allowing a user of the measuring device to recognize a difference from a correction chip having at least one structural characterizing portion thereon, the correction chip being for correcting errors in the measuring device, wherein said at least one structural characterization portion of said check chip is a plurality of structural characterization portions, the difference between said check chip and the correction chip residing in that said check chip is provided with at least one of said plurality of structural characterizing portions on each of two sides of said check chip, while the correction chip is provided with the at least one structural characterizing portion only on one side of the correction chip.

2. A check chip to be mounted on a measuring device to check operations of the measuring device, said check chip comprising a sensor body with a plurality of structural characterizing portions provided thereon which allows a user of the measuring device to recognize a difference from a correction chip for correcting errors in the measuring device, wherein said sensor body has an attention attracting character printed on an upside thereof, and one of said plurality of structural characterizing portions has optical penetrability and is located on said attention attracting character.

3. A check chip to be mounted on a measuring device to check operations of the measuring device, said check chip comprising a sensor body with at least one structural characterizing portion provided thereon, said at least one structural characterizing portion allowing a user of the measuring device to recognize a difference from a correction chip having at least one structural characterizing portion thereon, the correction chip being for correcting errors in the measuring device, wherein said at least one structural characterizing portion has a shape which can be recognized by the user from touch, and said at least one structural characterizing portion is provided in a location where the user is considered to pick said check chip up, and wherein said at least one structural characterizing portion of said check chip is a plurality of structural characterizing portions, the difference between said check chip and the correction chip residing in that said check chip is provided with at least one of said plurality of structural characterizing portions on each of two sides of said check chip, and the correction chip is provided with the at least one structural characterizing portion on only one side of the correction chip.

4. A check chip to be mounted on a measuring device to check operations of the measuring device, said check chip comprising a sensor body with at least one structural characterizing portion provided thereon, said at least one structural characterizing portion allowing a user of the measuring device to recognize a difference from a correction chip having at least one structural characterizing portion thereon, the correction chip being for correcting errors in the measuring device, wherein the difference between said check chip and the correction chip resides in a size of said at least one structural characterizing portion of said check chip, and wherein said at least one structural characterizing portion of said check chip is a plurality of structural characterizing portions, the difference between said check chip and the correction chip residing in that said check chip is provided with the at least one of said plurality of structural characterizing portions on each of two sides of said check chip while the correction chip is provided with the at least one structural characterizing portion on only one side of the correction chip.

5. A check chip to be mounted on a measuring device to check operations of the measuring device, said check chip comprising a sensor body with at least one structural characterizing portion provided thereon, said at least one structural characterizing portion allowing a user of the measuring device to recognize a difference from a correction chip having at least one structural characterizing portion thereon, the correction chip being for correcting errors in the measuring device, wherein the difference between said check chip and the correction chip resides in a size of said at least one structural characterizing portion of said check chip, wherein the size of said at least one structural characterizing portion provided on said check chip is larger than that of the structural characterizing portion provided on the correction chip, and wherein said at least one structural characterizing portion of said check chip is a plurality of structural characterizing portions, the difference between said check chip and the correction chip residing in that said check chip is provided with at least one of said plurality of structural characterizing portions on each of two sides of said check chip while the correction chip is provided with the at least one structural characterizing portion on only one side of the correction chip.

6. A check chip to be mounted on a measuring device to check operations of the measuring device, said check chip comprising a sensor body with at least one structural characterizing portion provided thereon, said at least one structural characterizing portion allowing a user of the measuring device to recognize a difference from a correction chip having at least one structural characterizing portion thereon, the correction chip being for correcting errors in the measuring device, wherein the difference between said check chip and the correction chip resides in a size of said at least one structural characterizing portion of said check chip, wherein the size of said at least one structural characterizing portion provided on said check chip is smaller than that of the structural characterizing portion provided on the correction chip, and wherein said at least one structural characterizing portion of said check chip is a plurality of structural characterizing portions, the difference between said check chip and the correction chip residing in that said check chip is provided with at least one of said plurality of structural characterizing portions on each of two sides of said check chip, while the correction chip is provided with the at least one structural characterizing portion on only one side of the correction chip.

7. A check chip to be mounted on a measuring device to check operations of the measuring device, said check chip comprising a sensor body with at least one structural characterizing portion provided thereon, said at least one structural characterizing portion allowing a user of the measuring device to recognize a difference from a correction chip having at least one structural characterizing portion thereon, the correction chip being for correcting errors in the measuring device, wherein said at least one structural characterizing portion has a shape which can be recognized by the user from touch, and said at least one structural characterizing portion is provided in a location where the user is considered to pick said check chip up, wherein the difference between said check chip and the correction chip resides in a size of said at least one structural characterizing portion of said check chip, and wherein said at least one structural characterizing portion of said check chip is a plurality of structural characterizing portions, the difference between said check chip and the correction chip residing in that said check chip is provided with at least one of said plurality of structural characterizing portions on each of two sides of said check chip while the correction chip is provided with the at least one structural characterizing portion on only one side of the correction chip.

8. A check chip to be mounted on a measuring device to check operations of the measuring device, said check chip comprising a sensor body with at least one structural characterizing portion provided thereon, said at least one structural characterizing portion allowing a user of the measuring device to recognize a difference from a correction chip having at least one structural characterizing portion thereon, the correction chip being for correcting errors in the measuring device, wherein said at least one structural characterizing portion has a shape which can be recognized by the user from touch, and said at least one structural characterizing portion is provided in a location where the user is considered to pick said check chip up, wherein the difference between said check chip and the correction chip resides in a size of said at least one structural characterizing portion of said check chip, wherein the size of said at least one structural characterizing portion provided on said check chip is larger than that of the structural characterizing portion provided on the correction chip, and wherein said at least one structural characterizing portion of said check chip is a plurality of structural characterizing portions, the difference between said check chip and the correction chip residing in that said check chip is provided with at least one of said plurality of structural characterizing portions on each of two sides of said check chip while the correction chip os provided with the at least one structural characterizing portion on only one side of the correction chip.

9. A kit for a measuring device, said kit comprising:

a correction chip adapted to be mounted on the measuring device to correct errors in the measuring device; and a check chip to be mounted on a measuring device to check operations of the measuring device, said check chip comprising a sensor body with at least one structural characterizing portion provided thereon which allows a user of the measuring device to recognize a difference from said correction chip, wherein said sensor body has an attention attracting character printed on an upside thereof, and said at least one structural characterizing portion has optical penetrability and is located on the attention attracting character.

* * * * *